(12) United States Patent
Liu et al.

(10) Patent No.: US 7,610,793 B2
(45) Date of Patent: Nov. 3, 2009

(54) RESIDENCE TIME CHAMBER AND SAMPLING APPARATUS

(75) Inventors: Zhili Gerald Liu, Madison, WI (US); Thaddeus Alan Swor, St. Paul, MN (US); James Alan Debilzen, Brooklyn, WI (US); Casey Lee Severance, Madison, WI (US)

(73) Assignee: Cummins Filtration IP Inc., Minneapolis, MN (US)

( * ) Notice: Subject to any disclaimer, the term of this patent is extended or adjusted under 35 U.S.C. 154(b) by 298 days.

(21) Appl. No.: 11/530,746

(22) Filed: Sep. 11, 2006

(65) Prior Publication Data

US 2008/0060457 A1    Mar. 13, 2008

(51) Int. Cl.
G01N 1/22 (2006.01)
G01N 1/26 (2006.01)
G01N 15/02 (2006.01)

(52) U.S. Cl. ............... 73/28.01; 73/863.31; 73/863.51; 73/864.73

(58) Field of Classification Search ............... 73/28.01, 73/863.31, 863.33, 864.73–864.74, 863.51
See application file for complete search history.

(56) References Cited

U.S. PATENT DOCUMENTS

| | | | |
|---|---|---|---|
| 3,457,787 A * | 7/1969 | Maatsch et al. | 73/863.31 X |
| 3,853,008 A * | 12/1974 | Hoffa et al. | 73/863.31 |
| 5,058,440 A | 10/1991 | Graze, Jr. | |
| 5,806,282 A * | 9/1998 | Hansen | 53/432 |
| 7,021,130 B2 | 4/2006 | Schmidt | 73/114.69 |
| 7,418,881 B2 | 9/2008 | Watson et al. | |

FOREIGN PATENT DOCUMENTS

FR    2670893 A1 *   6/1992   ............. 73/863.33
JP    2006226866 A *   8/2006

OTHER PUBLICATIONS

U.S. Appl. No. 11/530,728, filed Sep. 2006, Liu et al.
U.S. Appl. No. 11/530,758, filed Sep. 2006, Liu et al.
http://www.sciencedaily.com/releases/2006/06/060625124445.htm, 2 pages, Jun. 2006.

(Continued)

*Primary Examiner*—Thomas P Noland
(74) *Attorney, Agent, or Firm*—Hamre, Schumann, Mueller & Larson, P.C.; J. Bruce Schelkopf

(57) ABSTRACT

A residence time chamber and sampling apparatus for use in a system for sampling emission products from an emissions source, for example combustion engines including gasoline, diesel and natural gas engines, for subsequent measurement and analysis of the emission products. The results of the analysis can be used to formulate decisions on changes in engine design strategy, and can be used to determine the effectiveness of aftertreatment systems on the emissions source. The residence time chamber includes a plurality of isoaxial sampling probes, with a plurality of sampling trains connected to the sampling probes to take simultaneous representative emission samples for subsequent analysis. The residence time chamber minimizes many noise factors which can affect the accuracy of the test system, by applying isokinetic sampling and by reducing the interaction of the sampling gas and the particulate matter with the sampling probe inlets and with the various surfaces of the residence time chamber.

18 Claims, 7 Drawing Sheets

OTHER PUBLICATIONS

Hildeman et al., "Chemical Composition of Emissions from Urban Sources of Fine Organic Aerosol.", Environ. Sci. Technol., vol. 25, No. 4, 1991, pp. 744-759.

Hildeman et al., "A Dilution Stack Sampler For Collection of Organic Aerosol Emissions: Design, Characterization and Field Tests", Aerosol Science and Technology, vol. 10, 1989, pp. 193-204.

Kleeman et al., "Size and Composition Distribution of Fine Particulate Matter Emitted from Motor Vehicles", Environmental Science & Technology, vol. 34, No. 7, 2000, pp. 1132-1142.

Kweon et al., "Detailed Chemical Composition and Particle Size Assessment of Diesel Engine Exhaust," SAE 2002-01-2670, Fall SAE Meeting 2002, pp. 1-13.

Liu et al., "Transient Performance of Diesel Particulate Filters as Measured by an Engine Exhaust Particle Size Spectrometer", 2005-01-0185, 2005 SAE International, pp. 1-14.

Liu et al., "Transient Analysis of Engine Nano-Particles Using a Fast-Scanning Differential Mobility Particle Analyzer", 2004-01-0971, 2004 SAE International, pp. 1-10.

Liu et al., "Diesel Particulate Filters: Trends and Implications of Particle Size Distribution Measurement", 2003-01-0046, 2003 Society of Automotive Engineers, Inc., pp. 1-14.

MacGibbon et al., "The Effect of Thermophoresis on Particle Deposition in a Tungsten Low Pressure Chemical Vapor Deposition Reactor", Journal of The Electrochemical Society, vol. 146, No. 8, 1999, pp. 2901-2905.

Schauer et al., "Measurement of Emissions from Air Pollution Sources. 2. $C_1$ through $C_{30}$ Organic Compounds from Medium Duty Diesel Trucks", Environmental Science & Technology, vol. 33, No. 10, 1999, pp. 1578-1587.

"Performance Standards and Test Procedures for Automatic Isokinetic Samplers", Environment Agency, Version 1, Sep. 2005, pp. 1-12.

Office Action issued Nov. 26, 2008 in related U.S. Appl. No. 11/530,758.

\* cited by examiner

RESIDENCE TIME CHAMBER AND SAMPLING APPARATUS

FIELD

A residence time chamber and sampling apparatus for a system for sampling emission products from an emissions source, for example combustion engines including gasoline, diesel and natural gas engines, for subsequent measurement and analysis of the emission products.

BACKGROUND

Emissions of pollutant chemicals have increased by orders of magnitudes in the past 100 years due primarily to anthropogenic releases associated with industrial, agricultural, domestic, and recreational activity. Current research indicates that there are very strong correlations between the increase in these emissions and an overall increase in atmospheric temperatures (i.e. global warming) and an increased number of Category 4 and 5 hurricanes per annum. Furthermore, it is believed that ambient particulate matter in an aerosol phase may include potentially toxic components. Researchers also believe that particulate matter and gases from industrial activities and vehicles may cause various health problems, such as asthma. These correlations between emissions of pollutant chemicals and the negative impact on environment and human health has led to more stringent worldwide emission standards for automobiles and other vehicles, as well as power plants, mines, and other industries.

In the United States, emission standards are set by the Environmental Protection Agency (EPA) as well as state governments (e.g. California Air Resource Board (CARB)). As of this writing, all new vehicles sold in the United States must meet the EPA's "Tier 1" emission standard. A more stringent standard, "Tier 2," is being phased in for automobiles and should be completed by 2009. For diesel engines, on-road trucks and other vehicles will be required to meet more stringent standards by 2010 and off-road vehicles such as construction vehicles will be subject to Tier IV regulations. Accordingly, attaining ultra low emissions has become a top priority for combustion researchers as federal and state regulations continuously reduce the allowable levels of pollutants that can be discharged by engines, power plants, and other industrial processes.

In order to meet the emission standards of today and the future, researchers have made, and are continually striving to make, improvements to combustion engines, for example heavy duty diesel engines, gas combustion engines, power-generating gas turbines, and the like, and other emission sources. In addition to these developments, researchers are endeavoring for better methods and devices of measuring smaller particulate matter and quantifying the chemical compositions of trace emissions.

Generally, chemical composition analysis of fine particulate matter, inorganic gases, and volatile and semi-volatile organic compounds from emissions sources consists of three major steps: (1) Representative conditioning and sampling; (2) Chemical analysis; and (3) Data analysis and explanation. The effective accuracies of Steps (2) and (3) are both dependent on step (1). Without an accurate and precise sampling procedure, no analysis of that sample could be said to represent valid data. Accordingly, without valid analysis, a full and complete explanation of the sample would not be available.

In the United States, the typical system for assessing particulate matter mass emissions mixes emission gas with filtered air in a mixing chamber. The typical system is illustrated in FIG. 1, and includes a sampling port 2 that feeds exhaust gases to a diluter 4, forming the mixing chamber, where the exhaust gases are diluted with the filtered air. The diluted gas mixture is then sampled by a sampling train 6 to collect particulate matter mass. However, this typical system doesn't minimize a temperature gradient between sample gases and the inner wall of the mixing chamber and therefore may cause significant loss of sample particles during the dilution processes. In addition, the conventional system does not contain a separate residence time chamber which accurately reproduces the conditions under which ambient exhaust reaction products may form through both homogeneous and heterogeneous nucleation, condensation, and coagulation. Further, the conventional system allows only for assessment of single type of compound at one time. Accordingly, multiple sample runs are required to detect each of the chemical compounds necessary for a full compound assessment (trace elemental composition, ions, elemental carbon/organic carbon, polyaromatic hydrocarbons, semi-volatile organic compounds, etc.) Furthermore, not only is sample collection more time and resource consuming, but since these measurements are made with different sample runs, sampling errors may result, which can lead to inaccurate results.

Work at the University of Wisconsin-Madison attempted to improve on the conventional system. University of Wisconsin scientists used a device called an "augmented sampling system" to study the chemical composition and to assess particle size of diesel engine exhaust. See Chol-Bum Kweon, David E. Foster, James J. Schauer, and Shusuke Okada, "Detailed Chemical Composition and Particle Size Assessment of Diesel Engine Exhaust" SAE 2002-01-2670, Fall SAE Meeting 2002. The "augmented sampling system" disclosed by Kweon et al. includes a secondary dilution tunnel for the diesel exhaust and a residence time chamber with radial sampling ports near the base of a residence time chamber. The secondary dilution tunnel of the augmented sampling system mixes filtered air with an emission gas sample without regard to temperature gradient between the surface of the dilution tunnel and the emission gas. This may lead to a high degree of particle loss and accordingly less accurate sampling due to thermophoresis.

Thermophoresis, or Ludwig-Soret effect, is thought to be related to Brownian movement biased by a temperature gradient. The thermophoretic force is a force that arises from asymmetrical interactions of a particle with the surrounding gas molecules due to a temperature gradient. Generally, a particle is repelled from a hotter surface and attracted to a cooler surface. Thus, as emission particles travel through a sampling system, cooler surface temperature of the system as compared to the emission gas would lead to greater attraction on the emission particles.

In the Kweon et al. augmented sampling system, the residence time chamber is heated to reduce thermophoresis. However, the heated residence time chamber is likely to fail in simulating realistic atmospheric conditions, as the addition of heat may affect the aging, nucleation, condensation, and coagulation processes of particulate matter, volatile organic compounds and semi-volatile organic compounds and the secondary reaction of inorganic and organic compounds. In addition, the residence time chamber of Kweon et al. would not eliminate several sources of error introduced by boundary effects which occur between the gaseous fluid, with entrained particles, and the solid surfaces of the residence time chamber.

A residence time chamber and sampling apparatus for a system that allows more accurate and precise sampling of emission products is needed, thereby contributing to better measurement and analysis of the emission products and more accurate results.

SUMMARY

A residence time chamber and sampling apparatus is provided for a system used in sampling emission products from an emissions source, for example combustion engines including gasoline, diesel and natural gas engines, for subsequent measurement and analysis of the emission products. The residence time chamber and sampling apparatus have particular use in a system that is used to quantify emissions source species so that informed decisions on engine design strategy, and the effectiveness of aftertreatment systems, can be made.

The residence time chamber is designed to provide sufficient time for chemical specie equilibria to be established under conditions which closely simulate those which occur upon the mixing of exhaust emissions with air under actual ambient conditions. Reactions such as both homogeneous and heterogeneous nucleation, condensation, and coagulation occur in the residence time chamber, yielding the same reaction products as in actual ambient conditions, thereby yielding reliable information from which better design decisions may be made. Preferably, the residence time chamber is designed to provide a flow axis having a generally vertical orientation with at least 30 seconds of residence time under plug-flow conditions. During this time, chemical equilibria are established under laminar, or plug-flow, conditions yielding uniformly distributed specie concentrations while minimizing the boundary effects of chamber surfaces on the quantities of species present. The vertical orientation of the residence time chamber greatly reduces particulate matter losses due to the effects of gravity on the particles. The ends of the sampling probes are aligned coaxial to the flow direction within the residence time chamber (i.e. isoaxial) with the inlets of the probes facing into the direction of flow. This improves collection of the emission samples since the samples do not need to turn sharp corners to enter the probes.

Sampling rates through each sampling probe are controlled downstream by critical flow orifices or mass flow controllers in series with a rotary vacuum pump and manifold to achieve highly accurate isokinetic sampling. In isokinetic sampling, both the magnitude and direction of the velocity of the fluid being sampled remain unaltered at the sampling point, thus keeping aspiration efficiency unity and optimizing sampling.

In one embodiment, the sampling probe inlets are preferably located at least five sampling probe diameters from one another and from the residence time chamber wall to reduce surface boundary layer effects on samples. Another embodiment includes sampling probe inlets having thin walls (i.e. Do/Di<1.1) and sharp or tapered leading edges (angles<10 degrees), which also reduces boundary layer effects on the samples.

A plurality of sampling trains are connected to the sampling probes to permit the simultaneous sampling of different materials, including, but not limited to, volatile and semi-volatile organics, inorganic gases, and particulate matter mass and size samples.

In yet another embodiment, the residence time chamber includes a plurality of isoaxial sampling probes disposed inside the chamber. Further, a sampling train is connected to each of the isoaxial sampling probes.

DETAILED DESCRIPTION

Figure 1:
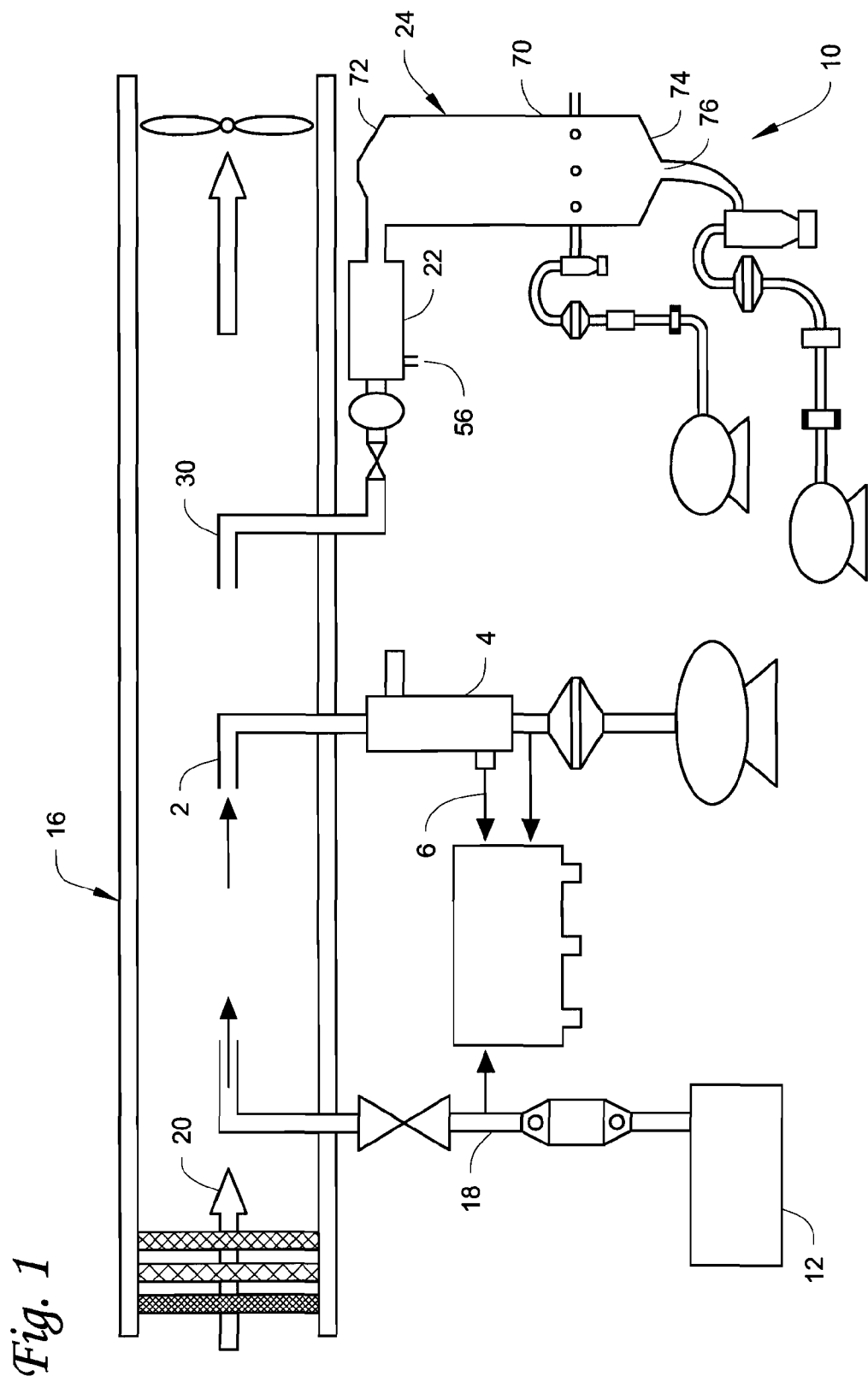
FIG. 1 illustrates a sampling system according to the invention connected to a primary dilution tunnel for sampling emissions from an engine.

With reference to FIG. 1, a system 10 for sampling emission products from an emissions source 12 is illustrated. The system 10 is constructed to simultaneously sample a number of different emissions products emitted from the emissions source 12. The samples can then be analyzed to permit chemical characterization of the emissions products.

The system 10 will be described herein as being applied to the sampling and chemical characterization of diesel emission exhaust from an emissions source 12 in the form of a diesel engine. However, the concepts described herein can be used to great advantage in sampling a number of other types of gases from a number of other types of emissions sources, both stationary and mobile. Examples of other types of gases includes, but it not limited to, gas combustion engine exhaust, turbine engine exhaust, and atmospheric gas. Examples of other types of emissions sources includes, but is not limited to, gas combustion engines, turbine engines, power plants, chemical plants, exhaust stacks, etc.

As shown in FIG. 1, the entire exhaust from the engine 12 is ducted to a dilution tunnel 16 through suitable piping 18. Filtered dilution air 20 is introduced into the tunnel upstream of the discharge for the engine exhaust, with the dilution air 20 then mixing with the engine exhaust in the tunnel 16 to dilute and cool the exhaust gas.

System

Figure 2:
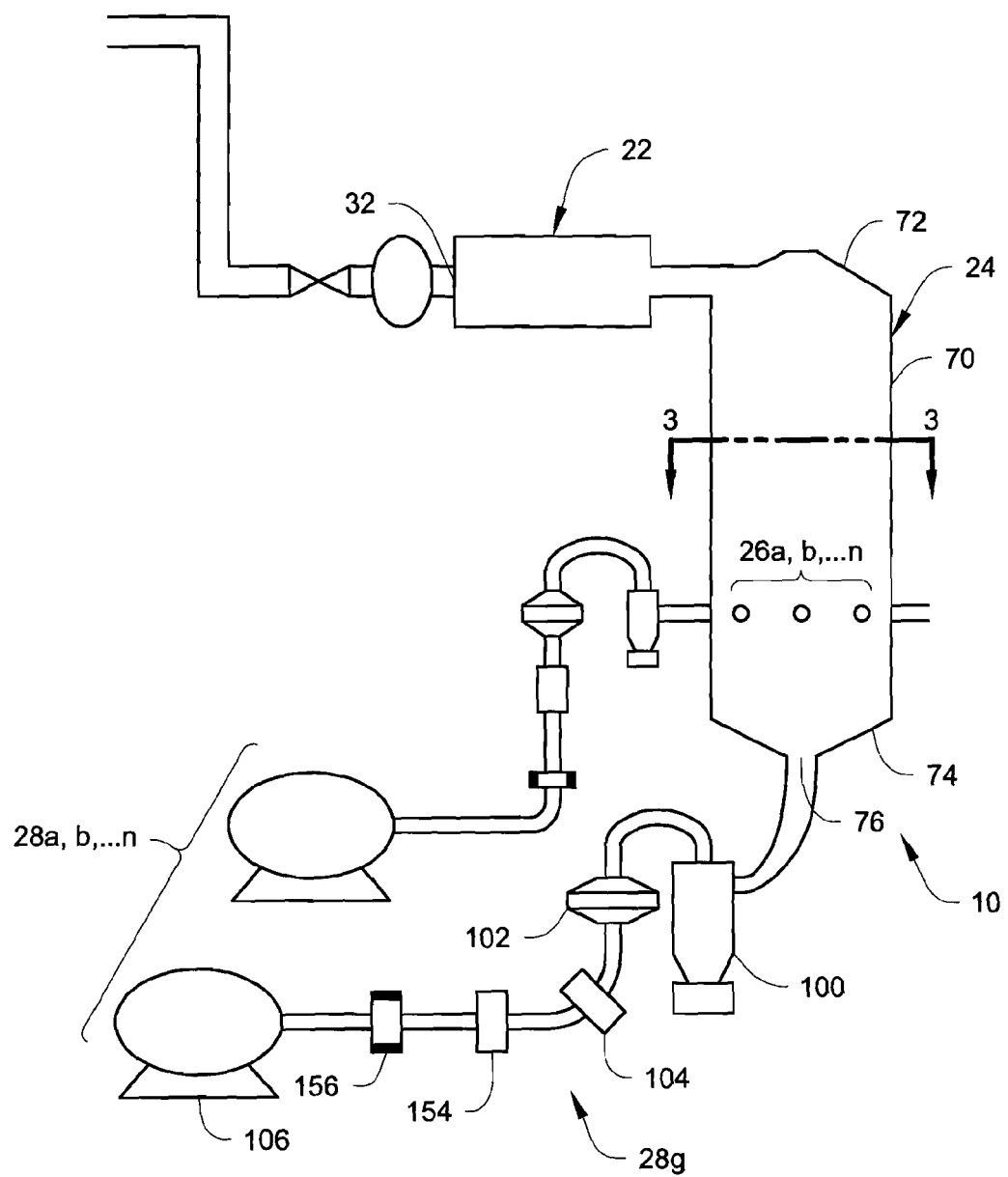
FIG. 2 illustrates the sampling system separate from the primary dilution tunnel.

With reference to FIGS. 1-2, the system 10 includes a dilution apparatus 22, a residence time chamber 24, a plurality of sampling probes 26a, b, . . . n (FIGS. 3-5) within the residence time chamber, and a plurality of sampling trains 28a, b, . . . n (FIGS. 6 and 7) connected to the sampling probes to take simultaneous representative emission samples for subsequent analysis.

The dilution apparatus 22 is connected to a sampling probe 30 that extends into the dilution tunnel 16. The probe 30 collects a gas stream sample from the engine 12 and directs the gas stream sample to the dilution apparatus 22. The inlet of the probe 30 is preferably positioned proximate the center of the dilution tunnel 16 to minimize boundary effects caused by the walls of the tunnel 16. In the dilution apparatus 22, the sampled gas is diluted with dilution gas, cooled to ambient temperature, and thoroughly mixed with the dilution gas.

The result is a full/partial/full dilution scheme, where the entire exhaust stream is initially diluted within the dilution tunnel 16, a portion of the exhaust stream is sampled by the sampling probe 30, and the entire portion of the gas sample is then diluted in the dilution apparatus. This full/partial/full dilution scheme is an improvement over conventional partial/full/partial dilution schemes, which direct only a portion of the exhaust stream into the dilution tunnel 16. As a result, more errors would be introduced due to two stages of partial dilution and sampling processes.

The gas mixture is then fed to the residence time chamber 24 which is designed to provide sufficient time for gas-to-particle conversion, which involves the diffusion limited transport of supersaturated vapor onto existing particles. The gas flow also becomes uniformly distributed before entering the sampling probes 26a, b, . . . n. The sampling probes 26a, b, . . . n simultaneously collect multiple samples of the gas mixture and feed the samples to the sampling trains 28a, b, . . . n which are constructed to take various samples of the gas. Preferably, the sampling trains are configured to sample chemical species within the gas samples, for example volatile and semi-volatile organics, gas-phase compounds, and particulate matter.

The components of the system 10 are preferably made of inert materials, including, but not limited to, stainless steel, plastic or polymer materials such as Teflon®, and plastic or polymer coated aluminum such as Teflon®-coated aluminum. In addition, the use of electrically non-chargeable materials, such as 304, 316 and 316L stainless steels, can also be used to reduce electrostatic deposition of charged particles that are typically polarized during combustion processes. In addition, the system 10 is preferably devoid of materials, for example oils, greases, rubbers and the like, that could outgas organics to avoid contamination of the gas stream and gas samples.

Further, the system 10 is preferably configured to minimize vapor and particulate losses. For example, the system is designed to promote smooth flow transitions within the system 10.

Further details on the overall system can be found in copending U.S. patent application Ser. No. 11/530,728, filed on Sep. 11, 2006, and titled Source Dilution Sampling System For Emissions Analysis, which application is incorporated herein by reference.

Further details on the dilution apparatus 22 can be found in copending U.S. patent application Ser. No. 11/530,758, filed on Sep. 11, 2006, and titled Thermophoretic-Resistant Gas Dilution Apparatus For Use In Emissions Analysis, which application is incorporated herein by reference.

Residence Time Chamber

The residence time chamber 24 is best illustrated in FIGS. 1-4. The chamber 24 includes a housing 70 having a first end 72 and a second end 74. In the illustrated embodiment, the housing 70 is oriented generally vertically so that the longitudinal axis of the housing 70 is oriented vertically and generally perpendicular to the longitudinal axis of the dilution apparatus 22 which is disposed generally horizontally.

The housing 70 is connected to the reducing cone 58 of the dilution apparatus 22 at the first end 72. Preferably, the first end 72 is in the form of a conical section, with the cone opening or facing downward. The gas mixture is received into the conical section 72, with the conical section helping to promote a smooth flow transition of the gas mixture from the dilution apparatus into the residence time chamber. Likewise, the second end 74 is in the form of a conical section, with the cone opening or facing upward. The conical section 74 helps to promote a smooth flow transition from the residence time chamber to an exit port 76 located at the bottom of the conical section 74.

The housing 70, except for the conical end sections 72, 74, is generally cylindrical and has a constant diameter between the first end 72 and the second end 74. The housing 70 provides sufficient time for gas-to-particle conversion within the gas mixture, and allows the gas flow to become uniformly distributed. Preferably, the housing 70 provides at least 30 seconds of residence time for the gas flow from the time the gas flow enters the housing 70 the time the gas flow reaches and enters one of the sampling probes. This residence time allows for quasi-static equilibrium of reaction product species to be achieved. The diameter and length of the residence time chamber are not only driven by the overall flow rate through the chamber to provide the 30 second residence time requirement, but are also driven by aerodynamic considerations. It is preferable to maintain laminar, or plug-flow, conditions inside the residence time chamber to reduce fluid turbulence and its associated boundary layer effects which negatively affect sample quality. This is achieved by maintaining a Reynolds number of less than about 2100. The Reynolds number is a dimensionless parameter which characterizes the level of turbulence in fluid systems and may be expressed as:

$$Re = V*D/v$$

Where:
V=temporal mean velocity of the fluid (in the vertical direction here)
D=the inside diameter of the residence time chamber
v=the kinematic viscosity, or momentum diffusivity, of the fluid.

Figure 6:
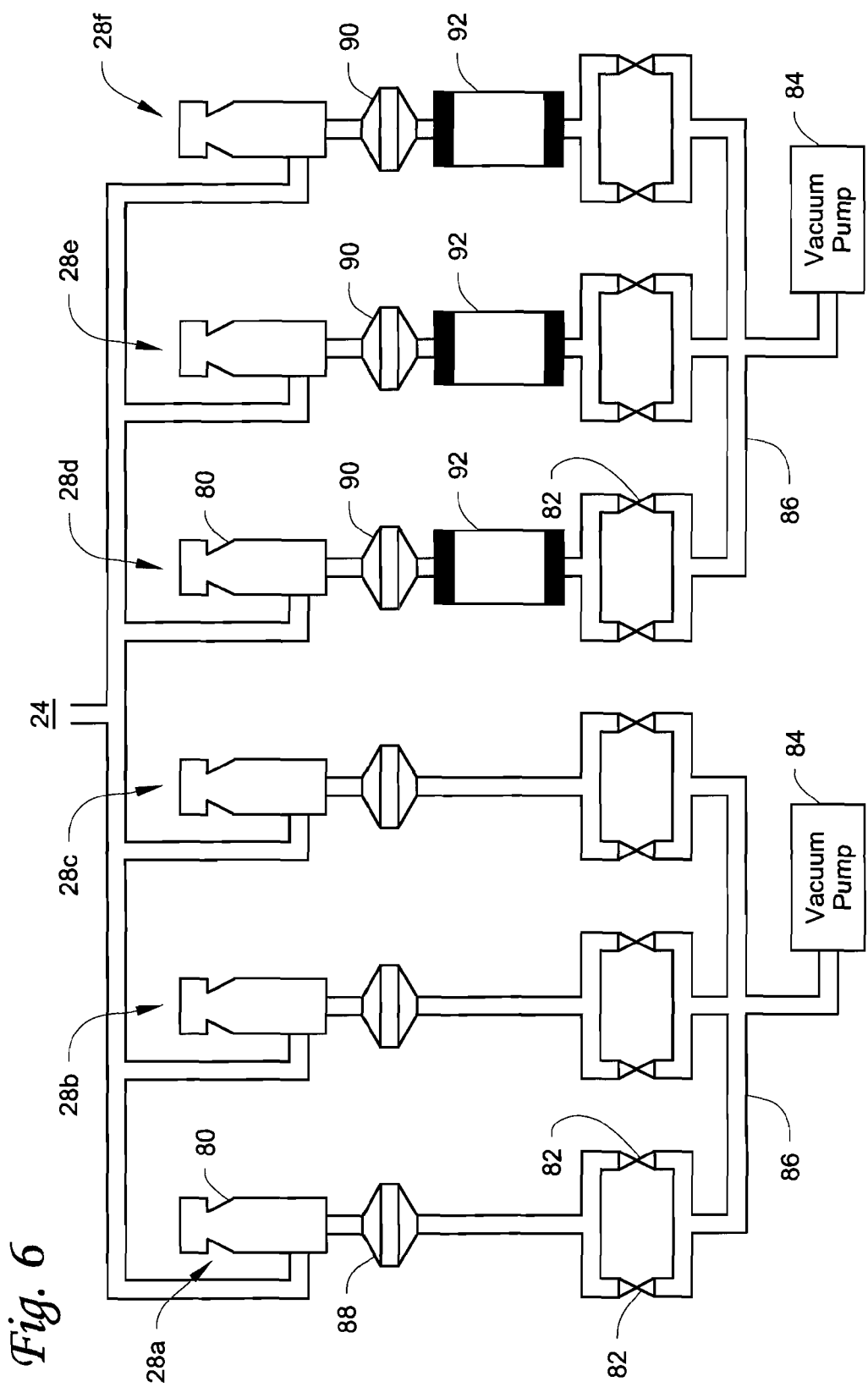
FIG. 6 is a schematic of various representative sampling trains.

If plug-flow conditions are maintained, the primary component of velocity of the fluid will be in the vertical (downward) direction. Not only does this minimize boundary layer effects which would result if turbulent flow interactions with the residence time chamber walls were allowed, but it also allows for effective isokinetic sampling. Isokinetic sampling is sampling where the fluid is withdrawn from the chamber without disturbing the overall flow pattern within the chamber. In other words, the sample is withdrawn from the chamber while the withdrawn fluid maintains the same velocity, both directionally and in magnitude, as that of the surrounding fluid. By maintaining plug-flow conditions, effective isokinetic sampling, where sampling probe surface interactions are minimized, may be achieved. The individual sampling probe flow rates are controlled downstream by critical flow orifices 82 or mass flow controllers in series with a rotary vacuum pump 84 via a manifold 86 as shown in FIGS. 1, 2, and 6.

Figure 3:
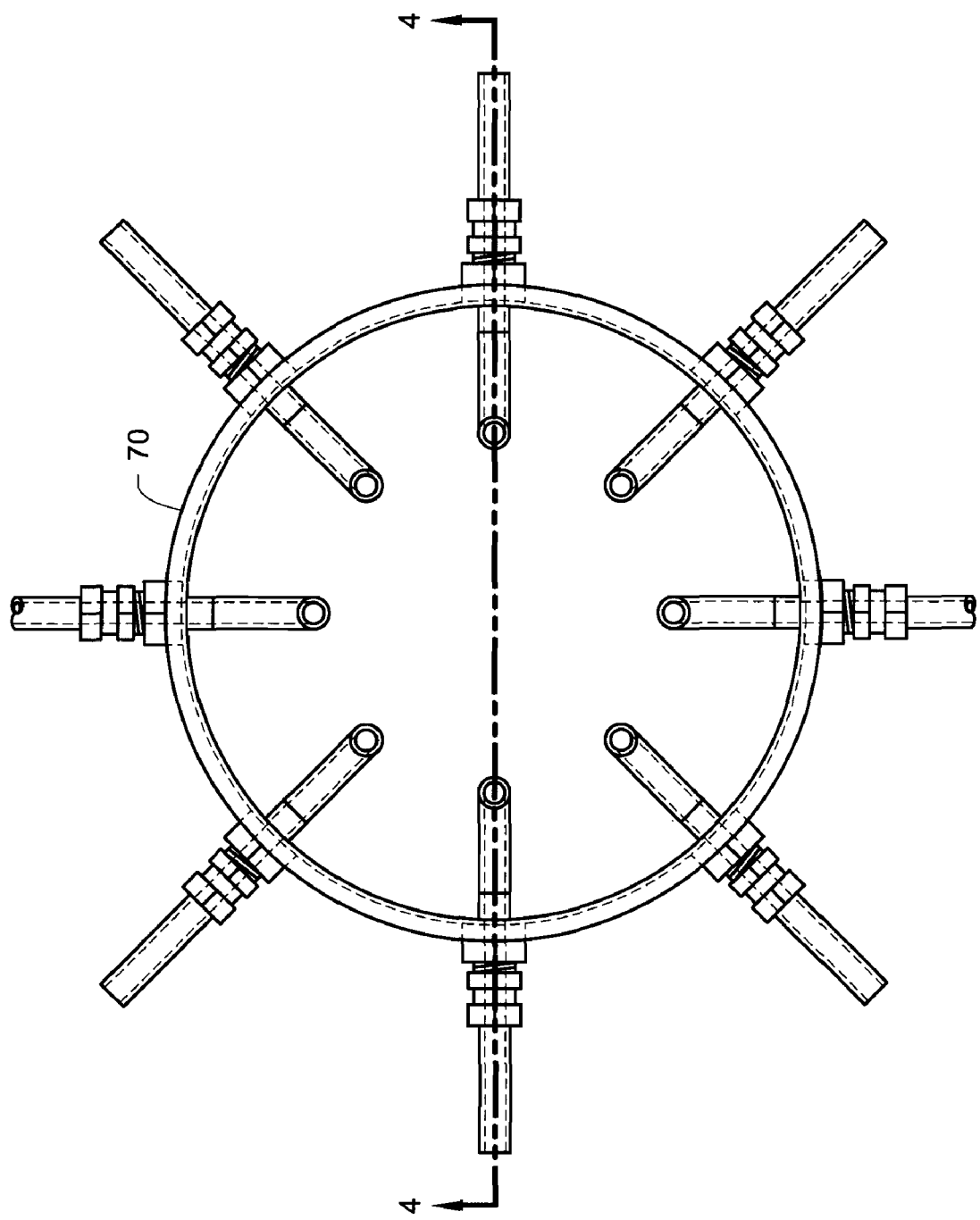
FIG. 3 is a cross-sectional view of the residence time chamber taken along line 3-3 in FIG. 2.
Figure 4:
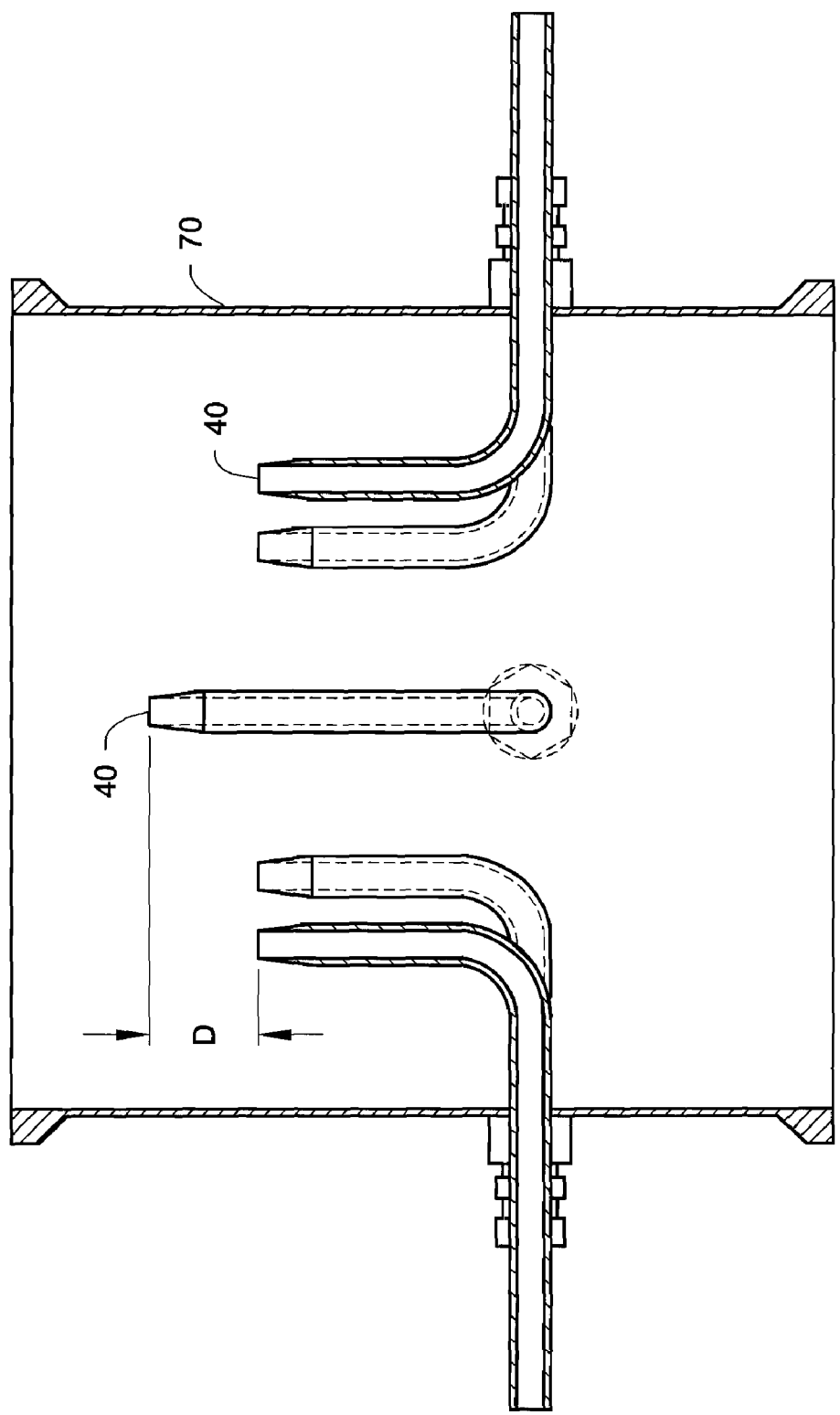
FIG. 4 is a cross-sectional view taken along line 4-4 in FIG. 3.

As shown in FIGS. 3 and 4, the sampling probes 26a, b, . . . n are disposed inside of the housing 70 to simultaneously collect multiple samples of the gas mixture and feed each sample to the sampling train 28a, b, . . . n. The inlets 40 of the sampling probes 26a, b, . . . n are aligned coaxial to the flow direction to achieve isoaxial and isokinetic sampling. In the illustrated embodiment, 8 sampling probes 26a, b, . . . n are provided, with each of the sampling probes 26a, b, . . . n extending upward with the inlets 40 to the probes facing upward toward the oncoming flow. To avoid boundary flow effects of the housing wall 70, the sampling probes 26a, b, . . . n are preferably spaced inwardly from the housing wall 70, and from each other, by a distance $D_L$. The distance $D_L$ is preferably at least about five sampling probe diameters, as shown in FIG. 3. The distance $D_L$ is calculated using the following equation:

$$D_L = \frac{ID/2 - r - \frac{r}{\cos(\theta)}}{\frac{1}{2\cos(\theta)} + 1}$$

where $D_L$=Distance between outside of sampling ports, distance from outside of sampling port to chamber wall
ID=Inner diameter of chamber
r=Inner radius of sampling port
θ=Half of obtuse angle between sampling ports=3*360 degrees/2*#ports Because the sampling probes 26a, b, . . . n are isoaxial with the residence time chamber 24, as shown in FIG. 4, and face upward toward the oncoming flow, sampling is improved because the sample flow does not need to turn sharp corners to enter the probes, thus allowing for isokinetic sampling, which reduces surface boundary layer effects, while simultaneously allowing for the accurate sampling of particulate matter.

Horizontally situated sampling probe inlets are undesirable because they not only preclude isokinetic sampling and introduce boundary layer effects, due to the abrupt changes in direction of the fluid being sampled, but also prevent accurate measurement of particulate matter because a horizontal suction would be required, which would further increase the boundary surface effects, to entrain the particulate matter.

Figure 5:
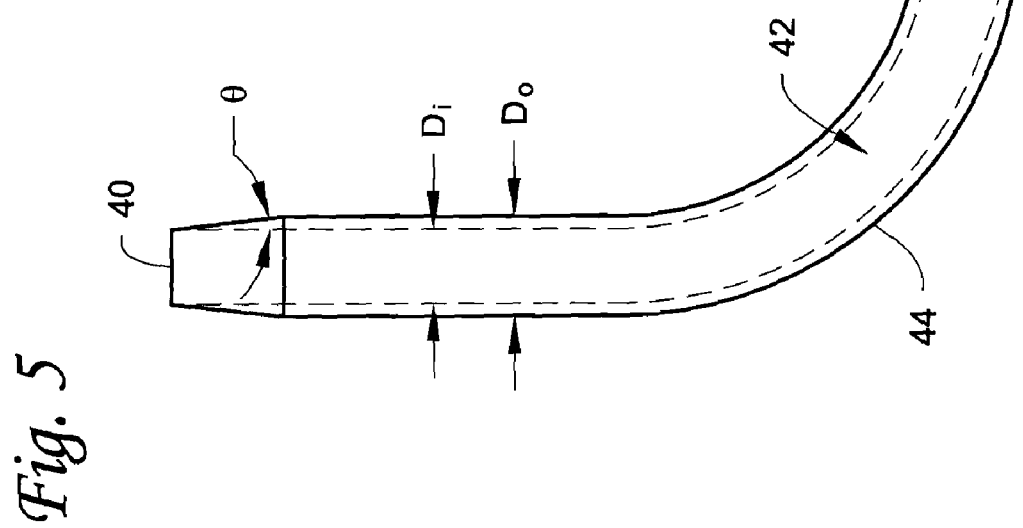
FIG. 5 is an enlarged detail view of a sampling probe.

An individual sampling probe 26 is depicted in FIG. 5. The sampling probe inlet 40 has thin wall where the outer diameter divided by the inner diameter (Do/Di) is less than 1.1, and a sharp or tapered leading edge which disturbs the plug-flow conditions as little as possible. Preferably, the taper θ of the leading edge is less than 15 degrees, and more preferably is less than about 10 degrees. Additionally, the sampling probes 26a, b, . . . n preferably extend vertically at least about four sampling probe diameters and then make a gradual arc of about 90 degrees in an intermediate portion 44 of the sampling probe 26 before exiting the residence time chamber 24. The radius 42 of this arc is preferably at least about four sampling probe diameters to help reduce surface boundary layer effects on the sample.

In one embodiment, shown in FIG. 4, interactions between high flow rate sampling and low flow rate sampling are avoided by placing the sampling probe inlets 40 at different horizontal levels, typically by placing the high flow rate sampling probe inlets below those in which a lower flow rate sampling is required. It is preferable to maintain a difference D in the sampling probe inlets heights from about 2 to about 6 sampling probe diameters, depending upon the sampling rate and the uniformity of the streamlines.

In another embodiment, different sampling probe flow rates may be achieved, while maintaining isokinetic conditions, by adjusting the diameter of each sampling probe accordingly.

Sampling Trains

The gas samples entering the sampling probes 26a, b, . . . n are directed to the sampling trains 28a, b, . . . n. The sampling trains can be configured to take samples of any kind of matter within the gas samples. Preferably, the sampling trains are configured to sample unregulated chemical species within the gas samples, for example volatile and semi-volatile organics, gas-phase compounds, and particular matter.

Figure 7:
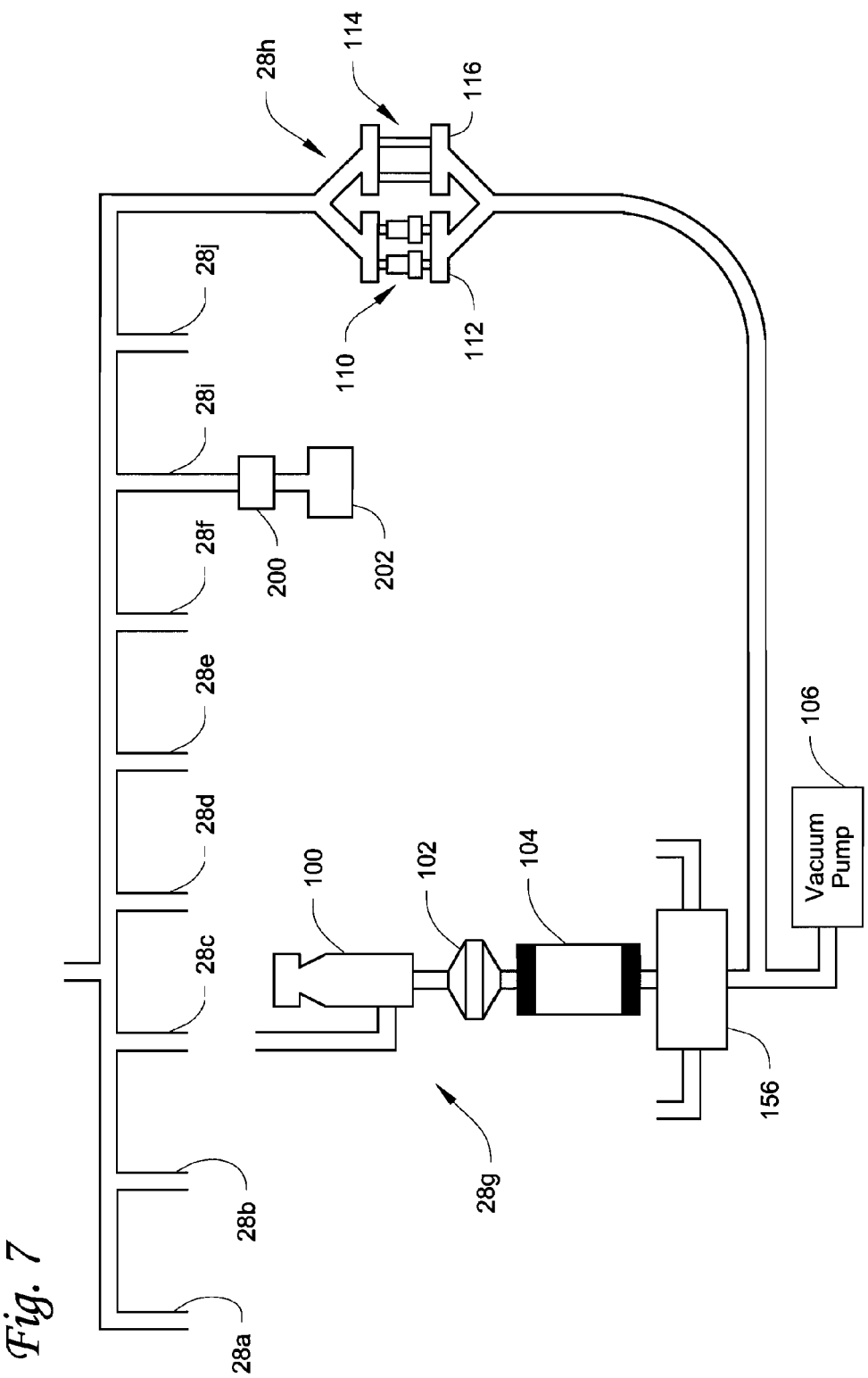
FIG. 7 is a schematic of a representative high flow sampling train and a representative gaseous sampling train.

Examples of suitable sampling trains are illustrated in FIGS. 6 and 7. As shown in FIG. 6, sampling trains 28a, 28b, 28c each begin with a PM2.5 cyclone separator 80 that can be operated at a flow rate of 16.7 liters/min (lpm) for removing particles that are about 2.5 microns and above. Flow through the trains 28a, 28b, 28c is controlled by downstream critical flow orifices 82 in series with a rotary vacuum pump 84 via a manifold 86. A rotameter prior to each critical flow orifice can be used to monitor the flow rate. A two stage filter holder 88, for example containing two Teflon® membrane filters, is disposed after the separator 80 to filter out material from the sampled gas. The filters 88 can then be analyzed for collected material. When the filters 88 are Teflon® membrane filters, analysis can be conducted for total mass, particulate matter sulfate ions, and particulate matter trace elemental composition.

The sampling trains 28d, 28e, 28f illustrated in FIG. 6 are similar to the sampling trains 28a, 28b, 28c. However, the illustrated trains 28d, 28e, 28f utilize filters 90, preferably quartz fiber filters, in series with a polyurethane foam (PUF) cartridge 92. An absorption material substrate, for example an XAD™ substrate, could be used in place of the PUF cartridge in the case of higher flow rates. When the filters 90 are quartz or TEFLON impregnated glass fiber (TIGF) filters, particle-phase organic compounds can be collected to analyze for particular matter organics, nitro-PAH particulate matter, and particulate matter hydrocarbon distribution. In the case of PUF cartridges, semi-volatile organic compounds can be collected to analyze for semi-volatile organic compounds, semi-volatile PAH and nitro-PAH, and semivolatile hydrocarbon distribution.

With reference to FIGS. 2 and 7, a sampling train 28g that is designed for high flow samples is illustrated. The sampling train 28g is connected to the exit port 76 at the bottom of the conical section 74. The sampling train 28g is not connected to a sampling probe. Instead, the sampling train samples the remainder of the gas flow that is not sampled by the sampling probes as the gas flow remainder exits through the bottom of the residence time chamber 24. The train 28g includes a PM2.5 cyclone separator 100 that can be operated at a flow rate of 92 liters/min (lpm) for removing particles that are about 2.5 microns and above, followed in series by a filter 102, for example a quartz or TIGF filter, a PUF cartridge 104 (or XAD substrate), critical flow orifices 156, and a rotary vacuum pump 106. This kind of sampling train 28g is suitable for use in collecting samples for polycyclic aromatic hydrocarbon analysis from low emission sources. The sampling train 28g can also include a flow meter 154, shown in FIG. 2.

With reference to FIG. 7, a sampling train 28g that is designed for high flow samples is illustrated. The train 28g includes a PM2.5 cyclone separator 100 that can be operated at a flow rate of 92 liters/min (lpm) for removing particles that are about 2.5 microns and above, followed in series by a filter(s) 102, for example a quartz or TIGF filter(s), a PUF cartridge(s) 104 (or XAD substrate(s)), critical flow orifices, and a rotary vacuum pump 106. This kind of sampling train 28g is suitable for use in collecting samples for polycyclic aromatic hydrocarbon (PAH) analysis from low emission sources.

FIG. 7 also illustrates a gaseous sampling train 28h which can be run in parallel to the sampling trains 28a-f. The sampling train 28h includes two Dinitrophenyl-Hydrazine (DNPH) cartridges 110 arranged in parallel to collect samples which are subsequently analyzed for carbonyl species. The cartridges 110 can have different flow rates, for example about 1.5 lpm and about 0.3 lpm. The flow rates can be controlled by critical flow orifices 112 in series with the rotary vacuum pump 106. In addition, the train 28h can include two volatile organic compound (VOC) tubes 114 arranged parallel to the DNPH cartridges to collect samples for hydrocarbon speciation. The flow rates through the VOC tubes 114 can range from about 10 standard cubic centimeters per minute (SCCM) to 50 SCCM, controlled by two separate mass flow controllers 116 in series with the vacuum pump 106. The mass flow controllers 116 can also be used to collect mass flow, volumetric flow, pressure, and temperature data. If desired, one or two filters prior to the DNPH cartridges 110 and VOC tubes 114 can be used to collect large particles.

As shown in FIG. 7, an additional sampling train 28i can be provided that sizes and counts particulate matter under steady state or transient conditions. For example, the sampling train 28i can include one or more particle sizers 200, for example scanning mobility particle sizers (SMPS), to measure particle size distributions and one or more particle counters 202, such as condensation particle counters (CPC's). In addition, an electrical low pressure impactor (ELPI) can be provided in the sampling train 28i. Further information on particulate matter sizing and counting can be found in: 1) "Transient Performance of Diesel Particulate Filters as Measured by an Engine Exhaust Particle Size Spectrometer", Z. Gerald Liu, Edward M. Thurow, Robert Caldow, and Timothy R. Johnson; 2005-01-0185; 2005 SAE International; 2) "Transient Analysis of Engine Nano-Particles Using a Fast-Scanning Differential Mobility Particle Analyzer", Z. Gerald Liu, Da-Ren Chen, Nalin Perera, George Pingen, Edward M. Thurow, and Joseph C. Lincoln, 2004-01-0971, 2004 SAE International; 3) "Diesel Particulate Filters: Trends and Implications of Particle Size Distribution Measurement", Z. Gerald Liu, Matthew D. Skemp and Joseph C. Lincoln, 2003-01-0046, 2003 Society of Automotive Engineers, Inc., which are incorporated herein by reference in their entirety.

In addition, a sampling train 28j can include temperature, humidity, and pressure sensors to monitor internal conditions of the residence time chamber.

Other types of sampling trains for collecting other types of materials within the sampled gas can be used. The sampling trains described herein are intended to be exemplary and not intended to be limiting.

The method of operation of the system 10 and of sampling exhaust gas from the engine 12 is apparent from the preceding description. A sample of the exhaust gas from the engine is initially directed into the dilution apparatus 22, through the sampling probe 30. Next, in the dilution apparatus, heat is exchanged between the gas sample and a dilution gas to cool the gas sample, and thereafter the dilution gas is introduced into the gas sample to mix with the gas stream sample and further cool the gas sample. The gas mixture is then directed to the residence time chamber, and a sample, preferably a plurality of simultaneous samples, of the gas mixture is taken from the residence time chamber through a sampling probe having an inlet substantially parallel to a direction of flow of the gas mixture within the residence time chamber. The sample is then directed to a sampling train which is configured to remove a desired material from the sample for subsequent analysis.

The invention may be embodied in other forms without departing from the spirit or novel characteristics thereof. The embodiments disclosed in this application are to be considered in all respects as illustrative and not limitative. The scope of the invention is indicated by the appended claims rather than by the foregoing description; and all changes which come within the meaning and range of equivalency of the claims are intended to be embraced therein.

The invention claimed is:

1. A gas stream residence chamber and sampling apparatus, comprising:
    a housing having a first end, a second end, and an axis extending from the first end to the second end, the axis aligned in a generally vertical orientation;
    a plurality of sampling probes within the housing, each sampling probe having an entrance portion defining an inlet with an inlet axis aligned with the axis of the housing; and
    wherein each inlet includes a diameter, and the inlets are each positioned more than five times their diameter from an inner wall of the housing and an outer surface of an adjacent sampling probe.

2. The gas stream residence chamber and sampling apparatus of claim 1, wherein each inlet is tapered.

3. The gas stream residence chamber and sampling apparatus of claim 2, wherein the taper of each inlet is less than 10 degrees.

4. The gas stream residence chamber and sampling apparatus of claim 1, wherein there are at least three of the sampling probes, and samples are taken from the three sampling probes simultaneously.

5. The gas stream residence chamber and sampling apparatus of claim 1, further comprising a sampling train in communication with each of the sampling probes.

6. The gas stream residence chamber and sampling apparatus of claim 5, wherein at least one of the sampling trains sizes and counts particulate matter under steady-state or transient conditions.

7. The gas stream residence chamber and sampling apparatus of claim 1, wherein the inlets of the sampling probes are disposed at different heights within the housing.

8. The gas stream residence chamber and sampling apparatus of claim 1, wherein the sampling probe inlets have thin walls.

9. A gas stream residence chamber and sampling apparatus, comprising:
    a housing having a first end, a second end, and an axis extending from the first end to the second end, the axis aligned in a generally vertical orientation;
    a plurality of sampling probes within the housing, each sampling probe having an entrance portion defining an inlet with an inlet axis aligned with the axis of the housing;
    each sampling probe includes a diameter, an exit portion, and an intermediate portion located between the entrance portion and the exit portion; each exit portion including an exit axis wherein each exit axis is generally perpendicular to each inlet axis, and each intermediate portion includes an arced portion with a bend radius of at least four times the diameter of the sampling probe.

10. The gas stream residence chamber and sampling apparatus of claim 9, wherein the sampling probes each have the same diameter.

11. A gas stream residence chamber and sampling apparatus, comprising:
    a housing having a first end, a second end, and an axis extending from the first end to the second end, the axis aligned in a generally vertical orientation;
    a plurality of sampling probes within the housing, each sampling probe having an entrance portion defining an inlet with an inlet axis aligned with the axis of the housing;
    wherein the sampling probes have entrance heights that are inversely proportional to the flow rate through each probe.

12. A gas stream residence chamber and sampling apparatus for a source dilution sampling system comprising:
a housing having a first end, a second end, and an axis extending from the first end to the second end; and
a plurality of isoaxial sampling probes within the housing for isoaxial sampling of a fluid stream within the housing, each sampling probe includes an inlet portion, a diameter, an exit portion, and an intermediate portion located between the inlet portion and the exit portion; each exit portion including an exit axis wherein each exit axis is generally perpendicular to each inlet axis, and each intermediate portion includes an arced portion with a bend radius of at least four times the diameter of the sampling probe.

13. The gas stream residence chamber and sampling apparatus of claim 12, wherein inlets of the inlet portions are spaced inwardly from an interior wall of the housing.

14. The gas stream residence chamber and sampling apparatus of claim 13, wherein at least some of the inlets are disposed at different heights within the housing.

15. The gas stream residence chamber and sampling apparatus of claim 13, wherein the sampling probe inlets have thin walls.

16. The gas stream residence chamber and sampling apparatus of claim 13, wherein the sampling probe inlets are tapered.

17. The gas stream residence chamber and sampling apparatus of claim 12, wherein the sampling probes have entrance heights that are inversely proportional to the flow rate through each probe.

18. The gas stream residence chamber and sampling apparatus of claim 13, wherein each inlet includes a diameter, and the inlets are each positioned more than five times their diameter from the interior wall of the housing and an outer surface of an adjacent sampling probe.

* * * * *